US009354038B2

(12) United States Patent
Yasuno et al.

(10) Patent No.: US 9,354,038 B2
(45) Date of Patent: May 31, 2016

(54) SWEPT SOURCE OPTICAL COHERENCE TOMOGRAPHY AND METHOD FOR STABILIZING PHASE THEREOF (71) Applicant: UNIVERSITY OF TSUKUBA, Tsukuba-shi, Ibaraki (JP)

(72) Inventors: Yoshiaki Yasuno, Tsukuba (JP); Masahide Itoh, Tsukuba (JP); Youngjoo Hong, Tsukuba (JP)

(73) Assignee: UNIVERSITY OF TSUKUBA, Tsukuba-Shi (JP)

( * ) Notice: Subject to any disclaimer, the term of this patent is extended or adjusted under 35 U.S.C. 154(b) by 18 days.

(21) Appl. No.: 14/368,456

(22) PCT Filed: Dec. 14, 2012

(86) PCT No.: PCT/JP2012/082460
§ 371 (c)(1),
(2) Date: Jun. 24, 2014

(87) PCT Pub. No.: WO2013/103080
PCT Pub. Date: Jul. 11, 2013

(65) Prior Publication Data
US 2015/0009507 A1 Jan. 8, 2015

(30) Foreign Application Priority Data
Jan. 5, 2012 (JP) ................. 2012-000313

(51) Int. Cl.
*G01B 9/02* (2006.01)
*A61B 3/10* (2006.01)
(Continued)

(52) U.S. Cl.
CPC ............ *G01B 9/02075* (2013.01); *A61B 3/102* (2013.01); *G01B 9/02001* (2013.01); *G01B 9/02083* (2013.01); *G01B 9/02091* (2013.01); *G01N 21/31* (2013.01); *G01N 21/4795* (2013.01)

(58) Field of Classification Search
CPC .... H01S 3/00; G01B 9/02004; G01B 9/0209; G01B 9/02091
USPC .................................................. 356/479, 497
See application file for complete search history.

(56) References Cited

U.S. PATENT DOCUMENTS 6,377,349 B1  4/2002  Fercher
2006/0244973 A1* 11/2006  Yun ...................... A61B 5/0059
                                                        356/511

(Continued)

FOREIGN PATENT DOCUMENTS

JP    H11-325849 A    11/1999
JP    2002-310897 A   10/2002
(Continued)

OTHER PUBLICATIONS

B. Vokoc et. al., "Phase-resolved optical frequency doma in imaging," OpticsExpress, Jul. 11, 2005, pp. 5483-5493, vol. 13, No. 14, Optical Society of America.

(Continued)

*Primary Examiner* — Jonathan Hansen
(74) *Attorney, Agent, or Firm* — Law Office of Katsuhiro Arai (57) ABSTRACT In an embodiment, a computer 16, which generates tomographic images based on spectral interference signals detected by a light detector 15 from overlaid reference light emitted by a swept-source type light source 2 of a SS-OCT, split, and then reflected by a fixed reference mirror 8 on one hand and object light reflected by an object to be measured 6 on the other, is caused to function to apply rough correction using a first correction means and then apply detailed correction using a second correction means, to stabilize the phases of the SS-OCT. The phases can be stabilized by eliminating, without adding any expensive, complex hardware, the jitter between the wavelength scanning of a light source of SS-OCT and the timing of collecting the scan data with the light detector as spectral interference signals.

8 Claims, 3 Drawing Sheets (51) Int. Cl.
　　*G01N 21/31*　　(2006.01)
　　*G01N 21/47*　　(2006.01)

(56) References Cited

U.S. PATENT DOCUMENTS

| 2006/0279742 | A1 | 12/2006 | Tearney et al. | |
| 2012/0053904 | A1* | 3/2012 | Yuasa | A61B 3/102 |
| | | | | 702/189 |
| 2013/0301000 | A1* | 11/2013 | Sharma | A61B 3/102 |
| | | | | 351/206 |

FOREIGN PATENT DOCUMENTS

| JP | 2004-028970 A | 1/2004 |
| JP | 2008-545970 A | 12/2008 |
| JP | 2010-014514 A | 1/2010 |

OTHER PUBLICATIONS

International Search Report (ISR) mailed Jan. 15, 2013, issued for International application No. PCT/JP2012/082460.

Hong, Y.-J. et.al., "High-penetration swept source Doppler optical coherence angiography by fully numerical phase stabilization", Optics Express, Jan. 23, 2012, pp. 2740-2760, vol. 20, Issue 3.

Tsai, M.-T. et. al., "Microvascular Imaging Using Swept-Source Optical Coherence Tomography Using Single-Channel Acquisition", Applied Physics Express, Aug. 12, 2011, pp. 097001-1-097001-3, vol. 4, No. 9, < DOI:10.1143 / APEX. 4. 097001 >.

* cited by examiner

Depth of object to be measured

Fig. 3
Background Art

SWEPT SOURCE OPTICAL COHERENCE TOMOGRAPHY AND METHOD FOR STABILIZING PHASE THEREOF This application is the U.S. National Phase under 35 U.S.C. §371 of International Application PCT/JP2012/082460, filed Dec. 14, 2012, which claims priorities to Japanese Patent Applications No. 2012-000313, filed Jan. 5, 2012. The International Application was published under PCT Article 21(2) in a language other than English.

TECHNICAL FIELD

The present invention relates to a swept source optical coherence tomography (abbreviated as SS-OCT) that scans the wavelengths of the light source to obtain spectral interference signals, as well as a method for stabilizing the phases of such swept source optical coherence tomography, and more specifically to a technology to stabilize phases using only the same configuration as that of any generally used SS-OCT, without using any additional hardware.

BACKGROUND ART

One non-destructive tomographic measurement technology used in the medical field, etc., is the optical coherence tomography (OCT) that uses light of temporally low coherence as a probe (refer to Patent Literature 1). As it uses light as a measurement probe, the OCT has the advantage of being able to measure the refractive index profile, spectral information, polarization information (birefringence index profile), etc. of the object to be measured.

Figure 3:
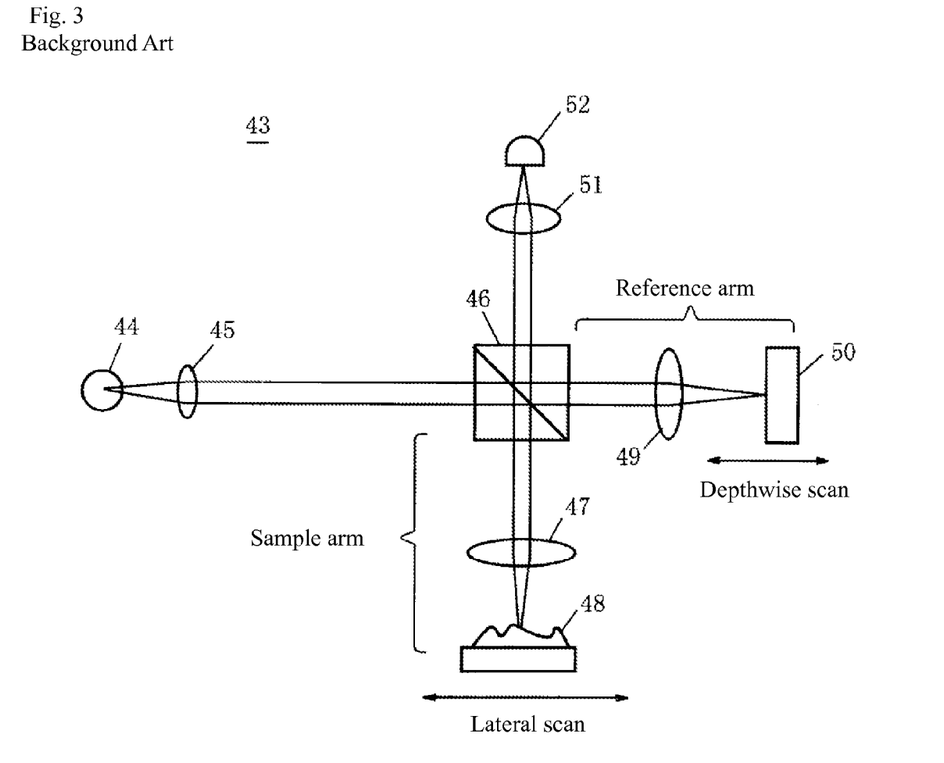
FIG. 3 Drawing explaining the conventional basic OCT.

A basic OCT 43 is based on Michelson's interferometer whose principles are explained using FIG. 3. Light emitted from a light source 44 is paralleled by a collimator lens 45 and then split into reference light and object light by a beam splitter 46. The object light is focused onto an object to be measured 48 by an objective lens 47 in the object arm, where it is scattered/reflected and then returned to the objective lens 47 and beam splitter 46.

On the other hand, the reference light passes through an objective lens 49 in the reference arm and then gets reflected by a reference mirror 50 and returns to the beam splitter 46 through the objective lens 49. The object light and reference light that have thus returned to the beam splitter 46 enter a condensing lens 51 and get focused onto a light detector 52 (photo-diode, etc.).

For the light source 44 of the OCT, a source of light of temporally low coherence (lights emitted from the light source at different times are extremely unlikely to interfere with each other) is used. With Michelson's interferometer that uses temporally low coherence light as its light source, interference signals manifest only when the distance from the reference arm is roughly equal to the distance from the sample arm. Accordingly, one can measure the intensities of interference signals using the light detector 52 while varying the optical path length difference ($\tau$) between the reference arm and sample arm to obtain interference signals at different optical path length differences (interferogram).

The shape of this interferogram represents the reflectance distribution of the object to be measured 48 in the depth direction, so the structure of the object to be measured 48 in the depth direction can be obtained by one-dimensional scan in the axial direction. With the OCT 43, therefore, the structure of the object to be measured 48 in the depth direction can be measured by scanning the optical path length.

A two-dimensional section image of the object to be measured can be obtained by a two-dimensional scan combining the aforementioned scan in the axial direction with a mechanical scan in the lateral direction. A scanner that performs this scan in the lateral direction may be configured, for example, to directly move the object to be measured, to shift the objective lens while keeping the object fixed, or to rotate the angle of the galvano-mirror placed near the pupil surface of the objective lens while keeping both the object to be measured and objective lens fixed.

An advanced version of the basic OCT mentioned above is the spectral domain OCT (SD-OCT) that obtains spectral signals using a spectrometer, and the swept source OCT (SS-OCT) that scans the wavelengths of the light source to obtain spectral interference signals. The SD-OCT has two types: the Fourier domain OCT (FD-OCT) (refer to Patent Literature 2) and the polarization-sensitive OCT (PS-OCT) (refer to Patent Literature 3).

The FD-OCT is characterized by obtaining the wavelength spectrum of reflected light from the object to be measured using the spectrometer and applying Fourier conversion to the intensity distribution of this spectrum to extract signals in the actual space (OCT signal space), thereby measuring the section structure of the object to be measured simply by scanning it in the x-axis direction, without having to scan it in the depth direction.

The SS-OCT obtains a three-dimensional optical tomographic image by rearranging and processing the interference signals using the light-source scanning signals obtained synchronously with the spectral signals by changing the wavelength of the light source with a high-speed swept source laser. The SS-OCT can also use a monochrometer as a means for changing the wavelength of the light source.

Retinal blood flow distribution measurement using the Doppler optical coherence tomography (Doppler OCT) is known. The Doppler-OCT provides a means for measuring the blood flow distribution in the retina using the aforementioned FD-OCT, etc., and by combining the Doppler-OCT with the spectral domain OCT, it becomes possible to form cross-section retinal blood flow images and also observe the dimensional vascular structure of the retina.

The inventors of the present invention had focused on the Doppler-OCT and studied and developed non-invasive ways to measure blood flows in a living body, especially those at the fundus of the eye. The inventors of the present invention had succeeded in inspecting the blood flows at the fundus of the eye by using the SD-OCT as the technical basis and installing the Doppler-OCT on it. However, the technical basis of OCT has been shifting from the SD-OCT to the next-generation technology SS-OCT in recent years.

PRIOR ART LITERATURES

Patent Literature

Patent Literature 1: Japanese Patent Laid-open No. 2002-310897
Patent Literature 2: Japanese Patent Laid-open No. Hei 11-325849
Patent Literature 3: Japanese Patent Laid-open No. 2004-028970

Non-Patent Literature

Non-patent Literature 1: B. Vokoc et. al., "Phase-resolved optical frequency doma in imaging," OpticsExpress 13, 5483-(2005).

SUMMARY OF THE INVENTION

Problems to be Solved by the Invention

The inventors of the present invention have also been studying and developing Doppler measurement using the SS-OCT, but this type of Doppler measurement presents a difficult problem. The problem is attributable to the phase instability specific to the SS-OCT.

A method to correct the phase instability of the SS-OCT has been proposed by the Harvard Medical School (refer to Non-patent Literature 1), but this technology requires complex hardware and thus leads to higher product cost.

The present invention is proposed to solve the aforementioned phase stabilization problem of the SS-OCT, and its object is to achieve higher phase stability by properly processing the signals obtained by using only the same conventional standard SS-OCT configuration, thereby realizing SS-OCT measurement and Doppler measurement using the conventional SS-OCT.

Means for Solving the Problems

To achieve the aforementioned object, the present invention provides a method for stabilizing the phases of SS-OCT which is a method for stabilizing the phases of spectral interference signals of a SS-OCT designed in such a way that reference light emitted from a swept-source type light source, split, and then reflected by a fixed reference mirror, is overlaid with object light reflected by an object to be measured and the overlaid lights are detected as spectral interference signals by a light detector, after which the phase data of spectral interference signals is corrected using a computer that generates tomographic images;

wherein such method is characterized in that: the correction of phase data of spectral interference signals is implemented by obtaining the spectral shift $\beta$ from the spectral interference signal $S_1(j)$ of the first A-scan used as a reference and also from the spectral interference signal $S'_2(j)$ which is a spectral interference signal of the second A-scan and to which the spectral shift $\beta$ has been applied due to jitter, where the two A-scans are adjacent to each other, according to equation (2') below and also using the reference light spectrum of the first A-scan as the reference spectral interference signal $S_1(j)$, and then by eliminating this spectral shift $\beta$, to correct the phase data of spectral interference signals.

$$\text{Angle}[F[S'_2(\zeta)]F[S_1*(\zeta)]]=-i2\pi\zeta\beta/N \qquad (2')$$

Here, N represents the number of sampling points, $\zeta$ is a variable indicating the depth of the object to be measured where $\zeta=0, 1, \ldots N-1$, $F[\ ]$ is an equation obtained by Fourier-converting the content of $[\ ]$, $\text{Angle}[\ ]$ is an equation indicating the phase in $[\ ]$, and * is a complex conjugate.

To achieve the aforementioned object, the present invention provides a method for stabilizing the phases of SS-OCT which is a method for stabilizing the phases of spectral interference signals of a SS-OCT designed in such a way that reference light emitted from a swept-source type light source, split, and then reflected by a fixed reference mirror, is overlaid with object light reflected by an object to be measured and the overlaid lights are detected as spectral interference signals by a light detector, after which the phase data of spectral interference signals is corrected sequentially by the first correction processing and second correction processing using a computer that generates tomographic images; wherein such method is characterized in that: the first correction processing involves: obtaining the spectral shift $\beta$ from the spectral interference signal $S_1(j)$ of the first A-scan used as a reference and also from the spectral interference signal $S'_2(j)$ which is a spectral interference signal of the second A-scan and to which the spectral shift $\beta$ has been applied due to jitter, where the two A-scans are adjacent to each other, according to equation (2') below and also using the reference light spectrum of the first A-scan as the reference spectral interference signal $S_1(j)$; and then eliminating this spectral shift $\beta$, to correct the phase data of spectral interference signals; and the second correction processing involves: solving the linear function where the intercept $b_m$ of $\zeta$ is $4\pi\tau v_b/\lambda_C$ and slope $a_m$ is $-2\pi\beta'/N$ in a region where there is no Doppler signal $v_z(\zeta)$, according to equation (9) below representing the Doppler phase shift pertaining to the spectral interference signals obtained by the two A-scans, to obtain the slope $a_m$ and intercept $b_m$ that give the smallest error energy as expressed by equation (10) below; and then obtaining the residual $\beta'$ of the spectral shift $\beta$ due to bulk motion and jitter, to correct the phase data of spectral interference signals.

$$\text{Angle}[F[S'_2(\zeta)]F[S_1*(\zeta)]]=-i2\pi\zeta\beta/N \qquad (2')$$

Here, N represents the number of sampling points, $\zeta$ is a variable indicating the depth of the object to be measured where $\zeta=0, 1, \ldots N-1$, $F[\ ]$ is an equation obtained by Fourier-converting the content of $[\ ]$, $\text{Angle}[\ ]$ is an equation indicating the phase in $[\ ]$, and * is a complex conjugate.

$$\Delta\phi(\zeta)=(4\pi\tau/\lambda_C)nv_z(\zeta)+(4\pi\tau/\lambda_C)v_b-2\pi\zeta\beta'/N \qquad (2')$$

Here, $\tau$ represents the interval between the two A-scans, $\lambda_C$ represents the center wavelength of the light source, n represents the refractive index, function $v_z(\zeta)$ of variable $\zeta$ represents the velocity in the optical axis direction, $v_b$ represents the bulk motion velocity, $\beta'$ represents the residual spectral shift due to jitter, N represents the number of sampling points, function $v_z(\zeta)$ of $\zeta$ represents the velocity in the optical axis direction, and $\zeta$ is a variable indicating the depth of the object to be measured where $\zeta=0, 1, \ldots N-1$.

$$R^2_2=\Sigma_\zeta W_m(\zeta)[\Delta\phi(\zeta)-(a_m\zeta+b_m)]^2 \qquad (10)$$

Here, m=0, 1, 2, C is a variable indicating the depth of the object to be measured, and $W_m(\zeta)$ is a weight.

To achieve the aforementioned object, the present invention provides a SS-OCT comprising a swept-source type light source, a light detector that detects the spectral interference signals of overlaid reference light emitted from the swept-source type light source, split, and then reflected by a fixed reference mirror, and object light reflected by an object to be measured, and a computer that generates tomographic images based on the spectral interference signals detected by the light detector; wherein such SS-OCT is characterized in that: the computer has a correction means for stabilizing the phases of the SS-OCT by correcting the phase data of spectral interference signals; and the correction means involves obtaining the spectral shift $\beta$ from the spectral interference signal $S_1(j)$ of the first A-scan used as a reference and also from the spectral interference signal $S'_2(j)$ which is a spectral interference signal of the second A-scan and to which the spectral shift $\beta$ has been applied due to jitter, where the two A-scans are adjacent to each other, according to equation (2') below and also using the reference light spectrum of the first A-scan as the reference spectral interference signal $S_1(j)$, and then by eliminating this spectral shift $\beta$ to correct the phase data of spectral interference signals.

$$\text{Angle}[F[S'_2(\zeta)]F[S_1*(\zeta)]]=-i2\pi\zeta\beta/N \qquad (2')$$

Here, N represents the number of sampling points, $\zeta$ is a variable indicating the depth of the object to be measured where ζ=0, 1, . . . N−1, F[ ] is an equation obtained by Fourier-converting the content of [ ], Angle[ ] is an equation indicating the phase in [ ], and * is a complex conjugate.

To achieve the aforementioned object, the present invention provides a SS-OCT comprising a swept-source type light source, a light detector that detects the spectral interference signals of overlaid reference light emitted from the swept-source type light source, split, and then reflected by a fixed reference mirror, and object light reflected by an object to be measured, and a computer that generates tomographic images based on the spectral interference signals detected by the light detector; wherein such SS-OCT is characterized in that: the computer has a first correction means and second correction means for stabilizing the phases of the SS-OCT by sequentially correcting the phase data of spectral interference signals; the first correction means involves: obtaining the spectral shift β from the spectral interference signal $S_1(j)$ of the first A-scan used as a reference and also from the spectral interference signal $S'_2(j)$ which is a spectral interference signal of the second A-scan and to which the spectral shift β has been applied due to jitter, where the two A-scans are adjacent to each other, according to equation (2') below and also using the reference light spectrum of the first A-scan as the reference spectral interference signal $S_1(j)$; and then eliminating this spectral shift β, to correct the phase data of spectral interference signals; and the second correction means involves: solving the linear function where the intercept $b_m$ of C is $4\pi\tau v_b/\lambda_C$ and slope $a_m$ is $-2\pi\beta'/N$ in a region where there is no Doppler signal $v_z(\zeta)$, according to equation (9) below representing the Doppler phase shift pertaining to the spectral interference signals obtained by the two A-scans, to obtain the slope $a_m$ and intercept $b_m$ that give the smallest error energy as expressed by equation (10) below; and then obtaining the residual β' of the spectral shift β due to bulk motion and jitter, to correct the phase data of spectral interference signals.

$$\mathrm{Angle}[F[S'_2(\zeta)]F[S_1^*(\zeta)]] = -i2\pi\zeta\beta/N \quad (2')$$

Here, N represents the number of sampling points, ζ is a variable indicating the depth of the object to be measured where ζ=0, 1, . . . N−1, F[ ] is an equation obtained by Fourier-converting the content of [ ], Angle[ ] is an equation indicating the phase in [ ], and * is a complex conjugate.

$$\Delta\phi(\zeta) = (4\pi\tau/\lambda_C)nv_z(\zeta) + (4\pi\tau/\lambda_C)v_b - 2\pi\zeta\beta'/N \quad (9)$$

Here, τ represents the interval between the two A-scans, $\lambda_C$ represents the center wavelength of the light source, n represents the refractive index, function $v_z(\zeta)$ of variable ζ represents the velocity in the optical axis direction, $v_b$ represents the bulk motion velocity, β' represents the residual spectral shift due to jitter, N represents the number of sampling points, function $v_z(\zeta)$ of ζ represents the velocity in the optical axis direction, and C is a variable indicating the depth of the object to be measured where ζ=0, 1, N−1.

$$R^2_2 = \Sigma_\zeta W_m(\zeta)[\Delta\phi(\zeta) - (a_m\zeta + b_m)]^2 \quad (10)$$

Here, m=0, 1, 2, C is a variable indicating the depth of the object to be measured, and $W_m(\zeta)$ is a weight.

Effects of the Invention

The following effects are achieved by the swept source optical coherence tomography and the method for stabilizing the phases of such swept source optical coherence tomography.

(1) Phases can be stabilized by using only the same configuration as that of any generally used SS-OCT, without additionally using a phase stabilization mirror, multi-channel digitizer or any other expensive, complex hardware.

(2) The time jitter (signal waveform fluctuation in the time axis direction based on a timing mismatch between the wavelength scanning of the light source on one hand, and the collection of spectral interference signals by the light detector on the other) of the spectral interference signals obtained from multiple A-scans (scans of the object to be measured in the depth direction) by the SS-OCT can be corrected.

(3) When a living body is captured by the SS-OCT, an artifact (false observation) in a Doppler signal caused by a movement of the living body (bulk motion) can be detected and corrected.

(4) When a living body is captured by the SS-OCT, the obtained Doppler shift information can be used to correct the time jitter with greater accuracy.

BEST MODE FOR CARRYING OUT THE PRESENT INVENTION

The best mode for carrying out a swept source optical coherence tomography and method for stabilizing the phases of such swept source optical coherence tomography, as they pertain to the present invention, is explained below based on an example by referring to the drawings.

First, the configuration of the main body of the SS-OCT (swept source optical coherence tomography) under the present invention is explained.

Figure 1:
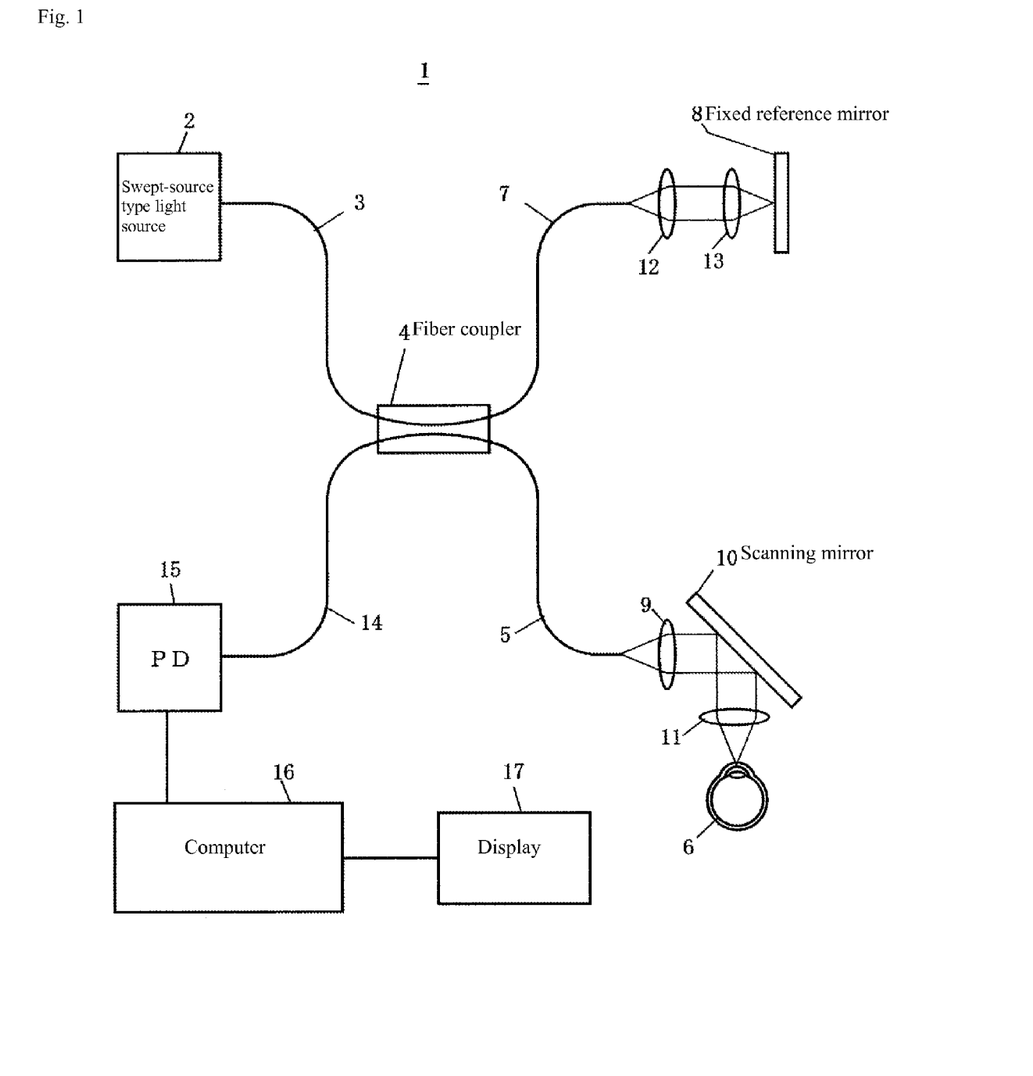
FIG. 1 Drawing showing the overall configuration of a PS-OCT system pertaining to the present invention.

FIG. 1 is a drawing showing the basic configuration of a SS-OCT 1. Output light emitted from a swept-source type light source 2 is sent to a fiber coupler 4 via a fiber 3. This output light is split by the fiber coupler 4 into object light which will be irradiated onto an object to be measured 6 via a fiber 5, and reference light which will be irradiated onto a fixed reference mirror 8 via a fiber 7.

Object light travels through the fiber 5, a lens 9, a variable-angle scanning mirror 10, and a lens 11, to be irradiated onto and reflected by the object to be measured 6, and then returns to the fiber coupler 4 along the same route. Reference light travels through the fiber 7, a lens 12 and a lens 13, to be irradiated onto and reflected by the fixed reference mirror 8, and then returns to the fiber coupler 4 along the same route.

Then, these object light and reference light are overlaid by the fiber coupler 4 and sent through a fiber 14 to a light detector 15 (a PD (photo-diode) or other point sensor is used), where they are detected as spectral interference signals and captured into a computer 16.

Section images of the object to be measured 6 in the depth direction (direction A) and in the scanning direction of the scanning mirror (direction B) are formed based on the detection output of the light detector 15. A display 17 is connected to the computer 16.

The swept-source type light source 2 is a light source that permits scanning of wavelengths varying temporally, that is to say, a light source whose wavelengths are time-dependent. This way, the reflectance distribution of the object to be measured 6 in the depth direction can be obtained without having to scan the fixed reference mirror 8 (scanning in the optical axis direction by moving in the optical axis direction) in order to perform A-scan (scanning of the object to be measured in the depth direction), to obtain the structure in the depth direction, meaning that a two-dimensional tomographic image can be formed by B-scan (scanning in the one-dimensional direction orthogonal to the optical axis direction) alone.

With the SS-OCT that scans by temporally varying the wavelength of its light source, a jitter (signal waveform fluctuation in the time axis direction and image disturbance resulting from this fluctuation) (caused by a mismatch) between the wavelength scanning of this light source (timing of change of wavelength) on one hand, and the timing at which data is collected by the light detector as spectral interference signals on the other, presents a problem.

This jitter causes random shifting in spectral sampling and consequently becomes a jitter of the spectral interference signals obtained by the SS-OCT.

In Doppler measurement, a Doppler signal is obtained according to the phase difference between the spectral interference signals from two A-scans (first A-scan $A_1$ and second A-scan $A_2$ obtained by B-scan), so the aforementioned jitter of the spectral interference signals obtained by the SS-OCT has direct impact on the data error in Doppler measurement.

The present invention relates to a method for stabilizing the phase data of spectral interference signals obtained by a SS-OCT using a computer that constitutes the SS-OCT (component of the SS-OCT), as well as a SS-OCT comprising the computer installed with a program that causes the computer to function as the correction means for stabilizing the phase data of spectral interference signals.

(Correction Means and Methods for Stabilizing Phase Data of SS-OCT)

Correction means and methods for stabilizing the phase data of the SS-OCT, as they pertain to the present invention, are such that a program that stabilizes the phase data of spectral interference signals of the SS-OCT is used to cause the computer of the SS-OCT to function as a means for performing the correction processing to stabilize the phase data of spectral interference signals, and do so in two stages including the first correction processing means and second correction processing means, thereby performing the first correction processing and second correction processing.

In the first correction processing by the first correction processing means, only the reference light of the SS-OCT is taken out as numerical values and the time correlation with respect to the optical spectrum of the SS-OCT is calculated from the numerical values, to correct rough spectral shifts of the spectral interference signals of the SS-OCT (or specifically jitters of the spectral interference signals of the SS-OCT).

In the second correction processing by the second correction processing means, spectral shifts caused by bulk motions (such as human eye movements, etc., that can produce artifacts (false observations) in the measured image) of the object to be measured is detected and corrected, to correct the phase data of the spectral interference signals of the SS-OCT with a higher level of performance compared to the first correction means.

Under the present invention, a program that stabilizes the phase data of the SS-OCT is installed in the computer constituting the SS-OCT, so that, as long as a method for stabilizing the phases of a swept source optical coherence tomography pertaining to the present invention is implemented, there is no need to add and use any expensive, complex device such as the phase stabilization mirror or multi-channel digitizer traditionally required.

The correction means and methods for stabilizing the phase data of the spectral interference signals of the SS-OCT, as they pertain to the present invention, are explained below together with the principles.

To clearly define the first correction processing means (correction means for rough spectral shift) and first correction processing, the applicable correction is explained below in concrete terms. Spectral interference signals of the SS-OCT are obtained by multiple A-scans (multiple A-scans performed by moving in the direction orthogonal to the direction of A-scan (i.e., by performing B-scan)), where the two spectral interference signals obtained by the two A-scans including the first A-scan $A_1$ and second A-scan $A_2$ are given as $S_1(j)$ and $S_2(j)$, respectively.

Here, j represents the spectral sampling point, or coordinate in the depth direction (optical axis direction) of A-scan, which is proportional to the wave number k. Here, when the wavelength is $\lambda$, frequency is f, and angular velocity is $\omega$, the relationship of $k\omega=\lambda f$ holds, meaning that the wave number k is expressed by $k=2\pi f$ based on $k=\lambda f/\omega$ and $f\omega=2\pi$.

Now, a relative spectral shift between the two spectral interference signals $S_1(j)$ and $S_2(j)$ is considered. Assume that a spectral shift $\beta$ due to a jitter was applied to the spectral interference signal $S_2(j)$ and $S_2(j)$ became $S'_2(j)$ as a result. In this case, $S'_2(j)$ is expressed by equation (1) below:

$$S'_2(j)=S_2(j)*\delta(j-\beta) \qquad (1)$$

Here, * represents a convolution.

When both sides of the equation are Fourier-converted, equation (2) below is obtained:

$$F[S'_2(\zeta)]=F[S_2(\zeta)]\exp(-i2\pi\zeta\beta/N) \qquad (2)$$

Here, F[ ] is an equation obtained by Fourier-converting the content of [ ]. N represents the number of sampling points, and $\zeta$ is a variable indicating the depth of the object to be measured where $\zeta=0, 1, \ldots N-1$. i represents the imaginary unit.

In Doppler measurement a Doppler signal is obtained according to the phase difference between the spectral interference signals from two A-scans, as mentioned above, but if the spectral interference signals from two A-scans have an identical shape, a jitter of the spectral interference signals has direct impact on the data error (phase error) of Doppler measurement.

If the spectral interference signals $S_1(j)$ and $S_2(j)$ from two A-scans match ($S_1(j)=S_2(j)$), the Doppler signal obtained from $S_1(j)$ and $S_2(j)$ has a phase error expressed by equation (2') below:

$$\text{Angle}[F[S'_2(\zeta)]F[S_1*(\zeta)]]=-i2\pi\zeta\beta/N \qquad (2')$$

Here, * is a complex conjugate, while Angle[ ] is an equation expressing the phase in [ ] (Angle[ ] itself represents the phase angle).

This equation indicates that, since the Doppler signal is linearly proportional to the spectral shift $\beta$, data of the Doppler signal expressed by this equation can be fitted using an applicable linear function to obtain the spectral shift $\beta$ caused by a jitter as the slope of this fitting function. It is also indicated that the effect of jitter can be removed by subtracting this fitted value from the Doppler signal.

In reality, however, an error does generate due to the factors listed below and accordingly the spectral data varies between the two A-scans:

(1) General error of each of the spectral interference signals $S_1(j)$ and $S_2(j)$ from the two A-scans
(2) Doppler shift caused by blood flow, etc.

(3) Error caused by a bulk motion (blurring or movement of a human eye or other similar test object that produces an artifact (false observation)), etc.

Accordingly, the present invention is characterized in that a computer is caused to function as a means for correcting the phase data of spectral interference signals using the spectral shift β obtained, in the case of the reference signal $S_1(j)$, by using the spectral data of reference light (signal returned from the reference light arm) free from error, etc., according to equation (2').

The foregoing constitutes the first correction processing means. When this means is explained in greater detail, the actually detected spectral interference signal $S_1(j)$ is expressed by equation (3) below:

$$S_1(j)=|E_r(j)|^2+|E_{p1}(j)|^2+E_r(j)E_{p1}*(j)+E_r*(j)E_{p1}(j). \quad (3)$$

Here, * is a complex conjugate. Also, $E_r(j)$ and $E_{p1}(j)$ represent the amplitudes of optical waves of the reference light and object light used in A-scan, respectively.

In this equation, the third term $E_r(j) E_{p1}*(j)$ and fourth term $E_r*(j) E_{p1}(j)$ are set to have a relatively high carrier frequency through adjustment of the optical system, while the first term $|E_r(j)|^2$ has a zero carrier frequency, and accordingly the third term and fourth term can be eliminated by means of numerical frequency filtering.

In addition, the $E_r(j) E_{p1}*(j)$ intensity of reference light is sufficiently greater than the intensity of object light in the case of the normal SS-OCT. In other words, the relationship of $|_r(j)^2>>|E_{p1}(j)|^2$ holds.

Accordingly, the spectral interference signal $S_1(j)$ can be rephrased as $S'_1(j)≈|E_r(j)|^2$. When Fourier conversion is applied, equation (4) below is obtained:

$$F[S'_1(j)]≈F[|E_r(j)|^2] \quad (4)$$

Here, F[ ] is an equation obtained by Fourier-converting the content of [ ].

In actual OCT measurement, $S'_2(j)$ is expressed by equation (5) below:

$$S'_2(j)=\{|E_r(j)|^2+|E_{p2}(j)|^2+E_r(j)E_{p2}(j)+E_r*(j)E_{p2}(j)\}*δ(j-β) \quad (5)$$

Here, * is a complex conjugate and * represents a convolution.

$E_{p2}(j)$ is the amplitude of probe light.

$S'_2(j)$ can be rephrased as the equation below based on approximation similar to the one applied to $S'_1(j)$:

$$S''_2(j)≈|E_r(j)|^2*δ(j-β)$$

When Fourier conversion is applied, equation (6) below is obtained:

$$F[S''_2(ζ)]≈F[|E_r(j)|^2]\exp(-i2πζβ/N) \quad (6)$$

Accordingly, the phase difference is expressed by equation (7) below:

$$F[S''_2(ζ)]F[S'_1*(ζ)]≈I(ζ)\exp(i2πζβ/N) \quad (7)$$

Here, $I(ζ)=F[|E_r(j)|^2]$ is an OCT intensity signal.

In theory, the phase of the error component, or $-i2πζβ/N$ in equation (7), should be a linear function of ζ. In reality, however, a shift from the linear slope is generated. This slope of phase β should be determined in such a way that the error expressed by equation (8) below becomes the smallest:

$$R^2_1=Σ_ζ[-2πζβ/N-φ(ζ)]^2 \quad (8)$$

Here, $φ(ζ)=∠F[S''_2(ζ)]F[S'_1*(ζ)]$ holds.

If the intensity I(ζ) is lower than the noise level, I(ζ) is set to 0. This way (as described above), any linear error component caused by a jitter can be numerically corrected.

The inventors of the present invention conducted an experiment to demonstrate the effectiveness of a method pertaining to the present invention and a SS-OCT adopting the method, by calculating the spectral shifts of two sets of spectral interference signals obtained under: a condition where the computer of the SS-OCT was installed with a program to implement the method pertaining to the present invention (program that causes the computer to function as a correction means for stabilizing the phase data of spectral interference signals obtained by the SS-OCT) and the first correction processing means was used; and another condition where such program was not installed and the first correction processing means was not used.

In this experiment, the standard deviation of phase differences was calculated, in the different depth directions, for the spectral interference signals obtained by adjacent A-scans, respectively.

Figure 2:
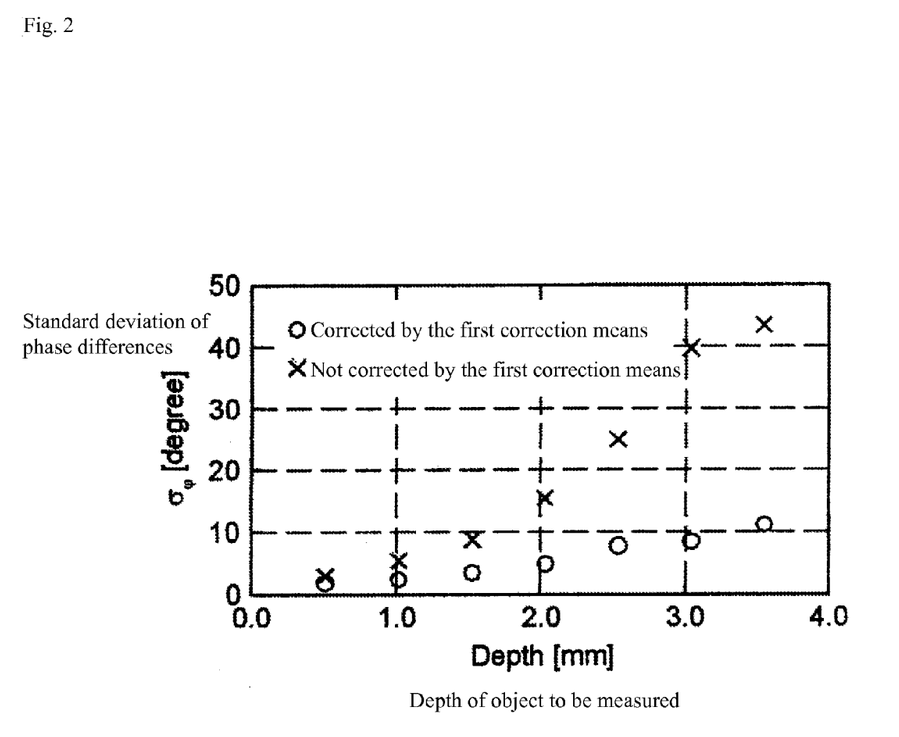
FIG. 2 Graph showing test results demonstrating the effectiveness of a method for stabilizing phases pertaining to the present invention and a SS-OCT adopting such method.

The result of this experiment is shown in FIG. 2. In FIG. 2, the horizontal axis represents the depth (unit: mm) of the object to be measured in the direction of A-scan, while the vertical axis represents the standard deviation ($σ_φ$) of phase differences of spectral interference signals in degrees. Also, the values denoted by ○ were calculated using the first correction processing means, while those denoted by × were calculated without using the first correction processing means.

According to the result of this experiment, the standard deviation of phase differences varied depending on the depth of the object to be measured in the direction of A-scan, regardless of whether or not the first correction processing means was used, where, specifically, the standard deviation of phase differences increased in deeper regions.

Then, when the first correction processing means was used, the standard deviation of phase differences became smaller than when it was not used. This substantiates that, when the first correction processing means is used, the standard deviation of phase differences of spectral interference signals becomes smaller over all regions in the depth direction of the object to be measured in the direction of A-scan and the phase stability improves as a result.

To clearly define the second correction processing means (correction means for residual spectral shift and bulk motion) and second correction processing, the applicable correction is explained below in concrete terms. The phase difference between the spectral interference signals obtained from adjacent A-scans that provide Doppler-OCT images is obtained as the phase component of the signal resulting from multiplying the complex conjugates of these adjacent A-scans (refer to equation (2') above).

Large spectral shifts near where the optical path difference between the reference light and object light is zero (zero delay point) can be corrected by the first correction processing means. However, an error (residual spectral shift) remains in signals far from the zero delay point. Also, bulk motions are not corrected.

Accordingly, in SS-OCT measurement the spectral interference signals are corrected further with "Doppler phase shift $Δφ(ζ)$" as expressed by equation (9) below, after they have been corrected by the first correction processing means:

$$Δφ(ζ)=(4πτ/λ_C)nv_z(ζ)+(4πτ/λ_C)v_b-2πζβ'/N \quad (9)$$

Here, τ represents the interval between the two A-scans, $λ_c$ represents the center wavelength of the light source, n represents the refractive index, function $v_z(ζ)$ of variable ζ represents the velocity in the optical axis direction, $v_b$ represents the bulk motion velocity, β' represents the residual spectral shift due to jitter, N represents the number of sampling points, function $v_z(\zeta)$ of $\zeta$ represents the velocity in the optical axis direction, and C is a variable indicating the depth of the object to be measured where $\zeta=0, 1, N-1$.

In this equation, the first term $(4\pi\tau/\lambda_c)nv_z(\zeta)$ is the Doppler signal to be measured. The second term $(4\pi\tau/\lambda_c)v_b$ is a signal due to bulk motion and a constant not dependent on the depth $\zeta$.

"$\beta'$" in the third term $-2\pi\zeta\beta'/N$ is the residual spectral shift due to jitter as mentioned above, but when the spectral shift $\beta$ not yet corrected by the first correction processing means is corrected by the first correction processing means, a majority of it is removed by the correction by the first correction processing means. Since the remaining residual $\beta'$ is small, $2\pi$ phase convolution does not occur here.

In a region where there is no Doppler signal $v_z(\zeta)$ (region where there is no movement of blood, etc.), the first term can be ignored and therefore $\Delta\phi(\zeta)$ in equation (9) becomes a linear function with an intercept of $\zeta$ of $4\pi\tau v_b/\lambda_c$ and slope of $-2\pi\beta'/N$.

This intercept and slope can be determined by obtaining, using the iterative method, the slope $a_m$ and intercept $b_m$ that give the smallest error energy as expressed by equation (10) below:

$$R^2{}_2 = \Sigma_\zeta W_m(\zeta)[\Delta\phi(\zeta)-(a_m\zeta+b_m)]^2 \quad (10)$$

Here, $m=0, 1, 2$, while $W_m(\zeta)$ is a weighting function indicating the importance of error in each $\zeta$ when the error energy is minimized using the iterative method.

As for iterative equation (10), the state of $m=0$, or initial value $W_0(\zeta)$, is expressed by equation (11) below:

If $I(\zeta) > \epsilon^2: W_0(\zeta) = (I(\zeta))^{1/2}$

Other than the above: $W_0(\zeta) = 0$ \quad (11)

Here, $I(\zeta)$ represents the OCT intensity signal, whiles $\epsilon$ represents the noise level.

The weight is refreshed using equation (12) below:

If $|\Delta\phi(\zeta)-(a_{m-1}\zeta+b_{m-1})| \geq \pi/2m: W_m(\zeta) = 0$

Other than the above: $W_m(\zeta) = W_{m-1}$ \quad (12)

Here, $m=1, 2$. In other words, the weight is zero if the error energy is smaller than a specified threshold, such as $7\pi/2$ m. If not, the weight is not refreshed. The threshold decreases as the number of repetitions m increases. The maximum value of m is determined beforehand (such as 6).

The foregoing explained, using an example, the best mode for carrying out a swept source optical coherence tomography and method for stabilizing the phases of such swept source optical coherence tomography pertaining to the present invention; however, the present invention is not at all limited to this example and it goes without saying that various examples are available within the scope of technical matters of the present application for patent as described in the claims.

INDUSTRIAL FIELD OF APPLICATION

A swept source optical coherence tomography and method for stabilizing the phases of such swept source optical coherence tomography pertaining to the present invention are useful in the inspection of blood flows at the fundus of the eye, permitting early detection of glaucoma and retinopathia diabetica. They also provide a useful tool for tumor imaging, allowing for three-dimensional visualization of new blood vessels around malignant tumors. Other promising applications include digestive system OCT and animal testing.

DESCRIPTION OF THE SYMBOLS

1 Swept source OCT
2 Swept-source type light source
3, 5, 7, 14 Fiber
4 Fiber coupler
6 Object to be measured
8 Fixed reference mirror
10 Scanning mirror
11, 12, 13 Lens
15 Light detector
17 Display

What is claimed is:

1. A method for stabilizing phases of SS-OCT (swept source optical coherence tomography) which is a method for stabilizing phases of spectral interference signals of a SS-OCT wherein reference light emitted from a swept-source type light source, split, and then reflected by a fixed reference mirror, is overlaid with object light reflected by an object to be measured and the overlaid lights are detected as spectral interference signals by a light detector, after which phase data of spectral interference signals is corrected using a computer that generates tomographic images; said method characterized by a correction of phase data of spectral interference signals and comprising:

obtaining a spectral shift $\beta$ from a spectral interference signal $S_1(j)$ of a first A-scan used as a reference and also from a spectral interference signal $S'_2(j)$ which is a spectral interference signal of a second A-scan and to which the spectral shift $\beta$ has been applied due to jitter, where the two A-scans are adjacent to each other, by determining a phase difference between a signal obtained by Fourier-converting the signal $S_1(j)$ and a signal obtained by Fourier-converting the signal $S'_2(j)$ and also by using a reference light spectrum of the first A-scan where the signal $S_1(j)$ is used as the reference spectral interference signal, and then eliminating this spectral shift $\beta$, thereby correcting the phase data of spectral interference signals.

2. A method for stabilizing phases of SS-OCT (swept source optical coherence tomography) which is a method for stabilizing phases of spectral interference signals of a SS-OCT wherein reference light emitted from a swept-source type light source, split, and then reflected by a fixed reference mirror, is overlaid with object light reflected by an object to be measured, and the overlaid lights are detected as spectral interference signals by a light detector, after which phase data of spectral interference signals is corrected sequentially by a first correction processing and a second correction processing using a computer that generates tomographic images; said method characterized by the first correction processing and the second correction processing, the first correction processing comprising:

obtaining a spectral shift $\beta$ from a spectral interference signal $S_1(j)$ of a first A-scan used as a reference and also from a spectral interference signal $S'_2(j)$ which is a spectral interference signal of a second A-scan and to which the spectral shift $\beta$ has been applied due to jitter, where the two A-scans are adjacent to each other, by determining a phase difference between a signal obtained by Fourier-converting the signal $S_1(j)$ and a signal obtained by Fourier-converting the signal $S'_2(j)$ and also by using a reference light spectrum of the first A-scan where the signal $S_1(j)$ is used as the reference spectral interference signal; and then eliminating this spectral shift $\beta$, thereby correcting the phase data of spectral interference signals; and the second correction processing comprising:
  solving a linear function where a Doppler phase shift pertaining to the spectral interference signals obtained by the two A-scans is a linear function of a depth position of the object to be measured in a region where no Doppler signal is measured, to obtain a slope and an intercept of the linear function that give a smallest error energy between the linear function and Doppler signals; and
  thereby obtaining a residual $\beta'$ of the spectral shift $\beta$ due to bulk motion and jitter, to correct the phase data of spectral interference signals.

3. A SS-OCT (swept source optical coherence tomography) comprising a swept-source type light source, a light detector that detects spectral interference signals of overlaid reference light emitted from the swept-source type light source, split, and then reflected by a fixed reference mirror, and object light reflected by an object to be measured, and a computer that generates tomographic images based on the spectral interference signals detected by the light detector; said SS-OCT characterized in that:
  the computer has a correction means for stabilizing phases of the SS-OCT by correcting phase data of spectral interference signals; and
  the correction means involves: obtaining a spectral shift $\beta$ from a spectral interference signal $S_1(j)$ of a first A-scan used as a reference and also from a spectral interference signal $S'_2(j)$ which is a spectral interference signal of a second A-scan and to which the spectral shift $\beta$ has been applied due to jitter, where the two A-scans are adjacent to each other, by determining a phase difference between a signal obtained by Fourier-converting the signal $S_1(j)$ and a signal obtained by Fourier-converting the signal $S'_2(j)$ and also by using a reference light spectrum of the first A-scan where the signal $S_1(j)$ is used as the reference spectral interference signal; and then eliminating this spectral shift $\beta$, to correct the phase data of spectral interference signals.

4. A SS-OCT (swept source optical coherence tomography) comprising a swept-source type light source, a light detector that detects the spectral interference signals of overlaid reference light emitted from the swept-source type light source, split, and then reflected by a fixed reference mirror, and object light reflected by an object to be measured, and a computer that generates tomographic images based on the spectral interference signals detected by the light detector; said SS-OCT characterized in that:
  the computer has a first correction means and a second correction means for stabilizing the phases of the SS-OCT by sequentially correcting phase data of spectral interference signals;
  the first correction means involves: obtaining a spectral shift $\beta$ from a spectral interference signal $S_1(j)$ of a first A-scan used as a reference and also from a spectral interference signal $S'_2(j)$ which is a spectral interference signal of a second A-scan and to which the spectral shift $\beta$ has been applied due to jitter, where the two A-scans are adjacent to each other, by determining a phase difference between a signal obtained by Fourier-converting the signal $S_1(j)$ and a signal obtained by Fourier-converting the signal $S'_2(j)$ and also by using a reference light spectrum of the first A-scan where the signal $S_1(j)$ is used as the reference spectral interference signal; and then eliminating this spectral shift $\beta$, to correct the phase data of spectral interference signals; and
  the second correction means involves solving a linear function where a Doppler phase shift pertaining to the spectral interference signals obtained by the two A-scans is a linear function of a depth position of the object to be measured in a region where no Doppler signal is measured, to obtain a slope and an intercept of the linear function that give a smallest error energy between the linear function and Doppler signals, and thereby obtaining a residual $\beta'$ of the spectral shift $\beta$ due to bulk motion and jitter, to correct the phase data of spectral interference signals.

5. The method according to claim 1, wherein the phase difference is determined according to an equation below:

$$\mathrm{Angle}[F[S'_2(\zeta)]F[S_1{}^*(\zeta)]]=-i2\pi\zeta\beta/N$$

wherein N represents a number of sampling points, $\zeta$ is a variable indicating a depth of the object to be measured where $\zeta=0, 1, \ldots N-1$, F[ ] is an equation obtained by Fourier-converting a content of [ ], Angle[ ] is an equation indicating a phase in [ ], and * is a complex conjugate.

6. The method according to claim 2, wherein the phase difference is determined according to an equation below:

$$\mathrm{Angle}[F[S'_2(\zeta)]F[S_1{}^*(\zeta)]]=-i2\pi\zeta\beta/N$$

wherein N represents a number of sampling points, $\zeta$ is a variable indicating a depth of the object to be measured where $\zeta=0, 1, \ldots N-1$, F[ ] is an equation obtained by Fourier-converting a content of [ ], Angle[ ] is an equation indicating a phase in [ ], and * is a complex conjugate, wherein the Doppler phase shift is represented by equation (2) below where an intercept $b_m$ of $\zeta$ is $4\pi\tau v_b/\lambda_c$ and a slope $a_m$ is $-2\pi\beta'/N$ in a region where there is no Doppler signal $v_z(\zeta)$, $$\Delta\phi(\zeta)=(4\pi\tau/\lambda_C)nv_z(\zeta)+(4\pi\tau/\lambda_C)v_b-2\pi\zeta\beta'/N \quad (2)$$

wherein $\tau$ represents an interval between the two A-scans, $\lambda c$ represents a center wavelength of the light source, n represents a refractive index, function $v_z(\zeta)$ of variable $\zeta$ represents a velocity in an optical axis direction, $v_b$ represents a bulk motion velocity, $\beta'$ represents the residual spectral shift due to jitter, N represents a number of sampling points, function $v_z(\zeta)$ of $\zeta$ represents the velocity in the optical axis direction, and $\zeta$ is a variable indicating a depth of the object to be measured where $\zeta=0, 1, \ldots, N-1$;

wherein the error energy is expressed by equation (3) below:

$$R^2{}_2=\Sigma_\zeta W_m(\zeta)[\Delta\phi(\zeta)-(a_m\zeta+b_m)]^2 \quad (3)$$

wherein $m=0, 1, 2 \ldots$, $\zeta$ is a variable indicating the depth of the object to be measured, and $W_m(\zeta)$ is a weight.

7. The SS-OCT according to claim 3, wherein the phase difference is determined according to an equation below:

$$\mathrm{Angle}[F[S'_2(\zeta)]F[S_1{}^*(\zeta)]]=-i2\pi\zeta\beta/N$$

wherein N represents a number of sampling points, $\zeta$ is a variable indicating a depth of the object to be measured where $\zeta=0, 1, \ldots N-1$, F[ ] is an equation obtained by Fourier-converting a content of [ ], Angle[ ] is an equation indicating a phase in [ ], and * is a complex conjugate.

8. The SS-OCT according to claim 4, wherein the phase difference is determined according to an equation below:

$$\text{Angle}[F[S'_2(\zeta)]F[S_1^*(\zeta)]] = -i2\pi\zeta\beta/N$$

wherein N represents a number of sampling points, $\zeta$ is a variable indicating a depth of the object to be measured where $\zeta=0, 1, \ldots N-1$, F[ ] is an equation obtained by Fourier-converting a content of [ ], Angle[ ] is an equation indicating a phase in [ ], and * is a complex conjugate, wherein the Doppler phase shift is represented by equation (2) below where an intercept $b_m$ of $\zeta$ is $4\pi\tau v_b/\lambda_c$ and a slope $a_m$ is $-2\pi\beta'/N$ in a region where there is no Doppler signal $v_z(\zeta)$, $$\Delta\phi(\zeta)=(4\pi\tau/\lambda_C)nv_z(\zeta)+(4\pi\tau/\lambda_C)v_b-2\pi\zeta\beta'/N \qquad (2)$$

wherein $\tau$ represents an interval between the two A-scans, $\lambda c$ represents a center wavelength of the light source, n represents a refractive index, function $v_z(\zeta)$ of variable $\zeta$ represents a velocity in an optical axis direction, $v_b$ represents a bulk motion velocity, $\beta'$ represents the residual spectral shift due to jitter, N represents a number of sampling points, function $v_z(\zeta)$ of $\zeta$ represents the velocity in the optical axis direction, and $\zeta$ is a variable indicating a depth of the object to be measured where $\zeta=0, 1, \ldots, N-1$;

wherein the error energy is expressed by equation (3) below:

$$R^2{}_2=\Sigma_\zeta W_m(\zeta)[\Delta\phi(\zeta)-(a_m\zeta+b_m)]^2 \qquad (3)$$

wherein m=0, 1, 2 ..., $\zeta$ is a variable indicating the depth of the object to be measured, and $W_m(\zeta)$ is a weight.

* * * * *